(12) United States Patent
Liphardt

(10) Patent No.: US 7,333,198 B1
(45) Date of Patent: *Feb. 19, 2008

(54) SAMPLE ORIENTATION SYSTEM AND METHOD

(75) Inventor: Martin M. Liphardt, Lincoln, NE (US)

(73) Assignee: J.A. Woollam Co., Inc., Lincoln, NE (US)

( * ) Notice: Subject to any disclaimer, the term of this patent is extended or adjusted under 35 U.S.C. 154(b) by 0 days.

This patent is subject to a terminal disclaimer.

(21) Appl. No.: 11/495,130

(22) Filed: Jul. 29, 2006

Related U.S. Application Data

(60) Division of application No. 11/177,207, filed on Jul. 8, 2005, now Pat. No. 7,084,978, which is a continuation-in-part of application No. 10/652,696, filed on Sep. 2, 2003, now Pat. No. 7,230,699.

(60) Provisional application No. 60/588,315, filed on Jul. 15, 2004, provisional application No. 60/459,690, filed on Apr. 3, 2003.

(51) Int. Cl.
*G01J 4/00* (2006.01)

(52) U.S. Cl. ..................................................... 356/364

(58) Field of Classification Search ............... 356/375, 356/369, 623, 399–401, 153
See application file for complete search history.

(56) References Cited

U.S. PATENT DOCUMENTS

| | | | | |
|---|---|---|---|---|
| 4,210,401 A | * | 7/1980 | Batten | 356/369 |
| 4,373,817 A | | 2/1983 | Coates | 356/636 |
| 5,045,704 A | | 9/1991 | Coates | 250/372 |
| RE34,783 E | | 11/1994 | Coates | 250/372 |
| 5,412,473 A | * | 5/1995 | Rosencwaig et al. | 356/369 |
| 5,486,701 A | | 1/1996 | Norton et al. | 250/372 |
| 5,596,411 A | | 1/1997 | Fanton et al. | 356/369 |
| 5,608,526 A | | 3/1997 | Piwonka-Corle | 356/369 |
| 5,771,094 A | * | 6/1998 | Carter et al. | 356/326 |
| 5,798,837 A | * | 8/1998 | Aspnes et al. | 356/369 |
| 5,889,593 A | | 3/1999 | Bareket et al. | 356/445 |
| 5,900,939 A | | 5/1999 | Aspnes et al. | 356/369 |
| 5,910,842 A | | 6/1999 | Piwonka-Corle | 356/369 |
| 6,091,499 A | | 7/2000 | Abraham et al. | 356/375 |
| 6,600,560 B2 | | 7/2003 | Mikkelsen et al. | 356/369 |
| 2002/0024668 A1 | | 2/2002 | Stehle et al. | |

OTHER PUBLICATIONS

PCT Publication WO 99/45340.

* cited by examiner

*Primary Examiner*—Tarifur Chowdhury
*Assistant Examiner*—Isiaka O Akanbi
(74) *Attorney, Agent, or Firm*—James D. Welch

(57) ABSTRACT

Disclosed are systems and methodology for orienting the vertical position, and tilt, of samples, as applied in ellipsometer and the like systems.

4 Claims, 4 Drawing Sheets

SAMPLE ORIENTATION SYSTEM AND METHOD

This Application is a Divisional of patent application Ser. No. 11/177,207 Filed Jul. 8, 2005 now U.S. Pat. No. 7,084,978 and therevia is a CIP of 10/652,696 Filed Sep. 2, 2003 now U.S. Pat. No. 7,230,699, and therevia Claims Benefit of Provisional Application Ser. No. 60/459,690 Filed Apr. 3, 2003. This Application also Claims Benefit of Provisional Application Ser. No. 60/588,315 Filed Jul. 15, 2004.

TECHNICAL FIELD

The disclosed invention relates to systems for adjusting sample orientation, and more particularly to systems and methods for orienting the vertical position, and tilt, of samples in ellipsometer and the like systems.

BACKGROUND

It is known to place samples on stages in ellipsometer and the like systems, and to cause a polarized beam of electromagnetic radiation to impinge on said sample at an oblique angle thereto, interact with said sample and then enter a detector. It is also known that the "tilt" of a sample surface at a specific location thereon can affect realized angle and plane of incidence values actually achieved. Further, it is known to adjust the vertical height of the stage to position a sample such that a beam of electromagnetic radiation reflecting therefrom enters a detector.

Existing Provisional and Utility Applications, (ie. 60/459,690 filed Apr. 3, 2003 and Ser. No. 10/652,696 filed Sep. 2, 2003), by the Inventor herein, show a prior art system for detecting sample tilt, and a system which utilizes an ellipsometer beam reflected from a sample to perform vertical positioning of a stage. A beam splitter is used to divert a portion of the reflected beam into a detector and used to mediate adjustment of the sample's vertical position and/or tilt. Said system does not secure relative position of the ellipsometer and sample, but provides for aligning a sample system and controlling the angle and plane of incidence at which a beam of electromagnetic radiation obliquely impinges on a monitored location of a surface of a sample, and comprises, as viewed in side elevation:

a sample supporting stage which can be translated in "X", "Y" or "Z" directions as well as rotated about "X", "Y" and optionally "Z" axes;

vertically above said stage there being a first beam splitter means, a lens and a first camera means for providing a view of a portion of the surface of said sample, said first beam splitter means optionally having positioned on a lower surface thereof light emitting means for providing light to the surface of said sample;

laterally with respect to said first beam splitter means there being a reflection means;

vertically above said reflection means there being a second beam splitter;

vertically above said second beam splitter there being a second camera means and laterally with respect to said second beam splitter, there being sequentially a lens and an essentially point source of electromagnetic radiation;

said first and second camera means each having associated therewith display means.

Said system further comprises an ellipsometer polarization state generator to cause, and a polarization stage detector to monitor, a beam of electromagnetic radiation which in use impinges on said monitored location on said surface of said sample at an oblique angle thereto.

In use said first camera means and its associated display means provide a view of at least a portion of the surface of a sample utilizing light provided by said light emitting means for providing light to the surface of said sample positioned on said lower surface of said first beam splitter, and said essentially point source of electromagnetic radiation provides electromagnetic radiation to the surface of said sample via said second beam splitter, said reflective means and said first beam splitter, and said sample supporting stage is caused to be translated in any of said "X", "Y" and "Z" directions as well as rotated about said "X", "Y" and optionally "Z" axes which are necessary to cause an interrogating beam of electromagnetic radiation provided by said essentially point source of a source of electromagnetic radiation to reflect from the surface of said sample, proceed back through said first beam splitter means, reflect from said reflective means, pass through said second beam splitter means, enter said second camera means and cause an image on the display means associated therewith which indicates that the monitored location on the sample surface is oriented so as to face substantially vertically.

The purpose of the foregoing is to align said sample surface to assure that said beam of electromagnetic radiation provided to said monitored location on the surface of said sample at an oblique angle approaches said surface at known intended angle of incidence and plane of incidence orientation, rather than at an angle of incidence and plane of incidence orientation which is modified by surface irregularities or non-flat samples.

Said system can further comprise a polarizer means in the path of said beam of electromagnetic radiation provided by said essentially point source of electromagnetic radiation, and in which said first beam splitter is sensitive to polarization state, and the polarizer means can be adjustable to enable control of the direction of polarization. The system point source of a source of electromagnetic radiation can comprise a fiber optic.

A patent to Abraham et al., U.S. Pat. No. 6,091,499 describes a method and system for automatic relative adjustment of samples in relation to an ellipsometer. Paraphrasing, said Abraham et al. system basically comprises:

a system for orienting a sample on a stage in an ellipsometer system comprising a first light source, a polarizer, said stage, an analyzer and a detector;

said system further comprising a detection system having a second light source, wherein said detection system is independently adjustable in relation to said ellipsometer, and wherein said detection system can be electronically locked into position relative to said ellipsometer so that said ellipsometer and said detection system can be adjusted as one unit in relationship to said stage, wherein said detection system can detect both a tilt of a sample placed onto said stage, and a distance of said sample from a coordinate source of the ellipsometer in two perpendicular axes; and said system further comprising an adjusting device, wherein said adjusting device can adjust tilt of said stage, and wherein said adjusting device can adjust the position of said ellipsometer and detection system when in an electronically locked relationship with respect to one another.

The 499 patent drawings show a single source, (identified as (21)), provides, via beam splitters and reflection means, normal and oblique angle of incidence electromagnetic beams to a sample, which normal and oblique angle of incidence electromagnetic beams are each intercepted by a different detector, (identified as (24) and (25) respectively), after reflecting from the sample. The associated ellipsometer system comprises a separate source, (identified as (11)).

Additional known patents are:
Coates U.S. Pat. No. 4,373,817;
Coates U.S. Pat. No. 5,045,704;
RE. 34,783 to Coates;
Mikkelsen et al., U.S. Pat. No. 6,600,560;
Fanton et al., U.S. Pat. No. 5,596,411;
Piwonka-Corle et al., U.S. Pat. No. 5,910,842;
Piwonka-Corle et al., U.S. Pat. No. 5,608,526;
Bareket U.S. Pat. No. 5,889,593;
Norton et al., U.S. Pat. No. 5,486,701;
Aspnes et al., U.S. Pat. No. 5,900,939;
PCT Application Publication WO 99/45340;
Published Application of Stehle et al., No. US2002/0024668 A1.

Need remains for additional systems and methods for orienting the vertical position, and tilt, of samples in ellipsometer, polarimeter, spectrophotometer and the like systems.

DISCLOSURE OF THE INVENTION

A system of the presently disclosed invention comprises means for causing electromagnetic radiation to impinge upon a sample along both substantially normal and oblique angles of incidence. Said electromagnetic radiation which impinges upon said sample at said oblique angle of incidence is caused to pass through focusing and collimating lenses before and after said sample respectively and said normal and oblique angle of incidence electromagnetic radiation being directed to enter the same or different detectors after interaction with said sample. Said system is characterized in that the length of the path of the electromagnetic radiation which impinges on said sample at an oblique angle of incidence, between said collimating lens and said detector to which it is directed is at least "X" times longer than the length of the path of said electromagnetic radiation between said sample and said collimating lens, where "X" is typically in the range of 2-10. The benefit of the identified "X" factor is that it acts as the equivalent of a "lever arm", to improve the system sensitivity to the height of a sample surface.

Further, said system can cause the electromagnetic radiation which is caused to approach said sample along both the normal and oblique angles of incidence are directed into a single detector, and typically there is at least one reflective electromagnetism reflective means in the pathway of the electromagnetic radiation which is caused to approach said sample along both the oblique angle of incidence to said sample. Where only one detector is present said system further comprises means for selectively directing only one selection from the group consisting of:

the electromagnetic radiation which is caused to approach said sample along the normal angle of incidence; and
the electromagnetic radiation which is caused to approach said sample along the oblique angle of incidence;
into said single detector at a time. Said means can be a shutter system.

A preferred system provides electromagnetic radiation which is caused to approach said sample along both the normal and oblique angles of incidence to be provided from a single source of electromagnetism.

Further, a preferred system provides that electromagnetic radiation intensity modulating means, (eg. a beam chopper), be present in the pathway of at least one selection from the group consisting of:

the electromagnetic radiation which is caused to approach said sample along the normal angle of incidence; and
the electromagnetic radiation which is caused to approach said sample along the oblique angle of incidence.

When intensity is modulated by such as a beam chopper, data can be obtained in a lite room without the external light adversely affecting the data signal.

Additional system description will be presented in the Detailed Description Section of this Specification as it is helpful to have reference to the Drawings.

The method of use of the presently disclosed invention involves adjusting the vertical location of the sample, and the tilt thereof until the alignment detector, or detectors, indicate proper alignment. It is noted that this does not require movement of an ellipsometer system applied to investigate a sample, or an adjusting device which is electronically coupled into a relationship with said ellipsometer.

More specifically, a disclosed invention method of investigating a sample comprising the steps of:

practicing steps a and b in either order:

a) providing an ellipsometer or the like system which sequentially comprises a source of a beam of electromagnetism, polarizer means for imposing a state of polarization on said beam, a stage for supporting a sample, analyzer means for selecting polarization states of a beam of electromagnetic radiation after it interacts with a specific location on a sample placed on said stage, and an ellipsometer detector;

b) providing a sample alignment system such that electromagnetic radiation produced thereby is caused to impinge on substantially the same point on said sample as does the ellipsometer beam, reflect therefrom both substantially normally and at an oblique angle, and enter at least one alignment detector;

c) using output from said at least one alignment detector provided in step b to effect vertical height and tilt alignment of the sample;

d) with the sample aligned, obtaining ellipsometric data from the ellipsometer detector;

e) analyzing said ellipsometer system data.

Said method can further comprise, in step b, providing an automatic alignment system which comprises means for receiving input from the alignment detector or detectors and automatically effecting sample vertical height and tilt alignment, and in step c the using of output from said alignment detector or detectors to effect automated vertical height and tilt alignment of the sample.

The disclosed invention will be better understood by reference to the Detailed Description Section of this Disclosure, in combination with the Drawings.

SUMMARY OF THE INVENTION

It is therefore a purpose and/or objective of the disclosed invention to teach systems and methods for orienting the vertical position, and tilt, of samples in ellipsometer and the like systems.

It is another purpose and/or objective of the disclosed invention to teach a system for increasing sensitivity to sample height monitoring which utilizes focusing and collimating lenses before and after a sample, respectively.

It is yet another purpose and/or objective of the disclosed invention to teach a system for increasing sensitivity to sample height monitoring which is based on a "lever arm" principal.

It is another purpose and/or objective yet of the disclosed invention to teach a system for monitoring sample height and tilt in the context of an ellipsometer system, in which only a single source of electromagnetism is utilized in said monitoring system and ellipsometer.

Other purposes and/or objectives of the disclosed invention will become apparent upon a reading of the Specification and Claims.

DETAILED DISCLOSURE OF THE INVENTION

The present disclosure is of new systems and methodology for alignment of both tilt, and vertical positioning, of samples, which systems are well suited for automated operation.

Figure 1:
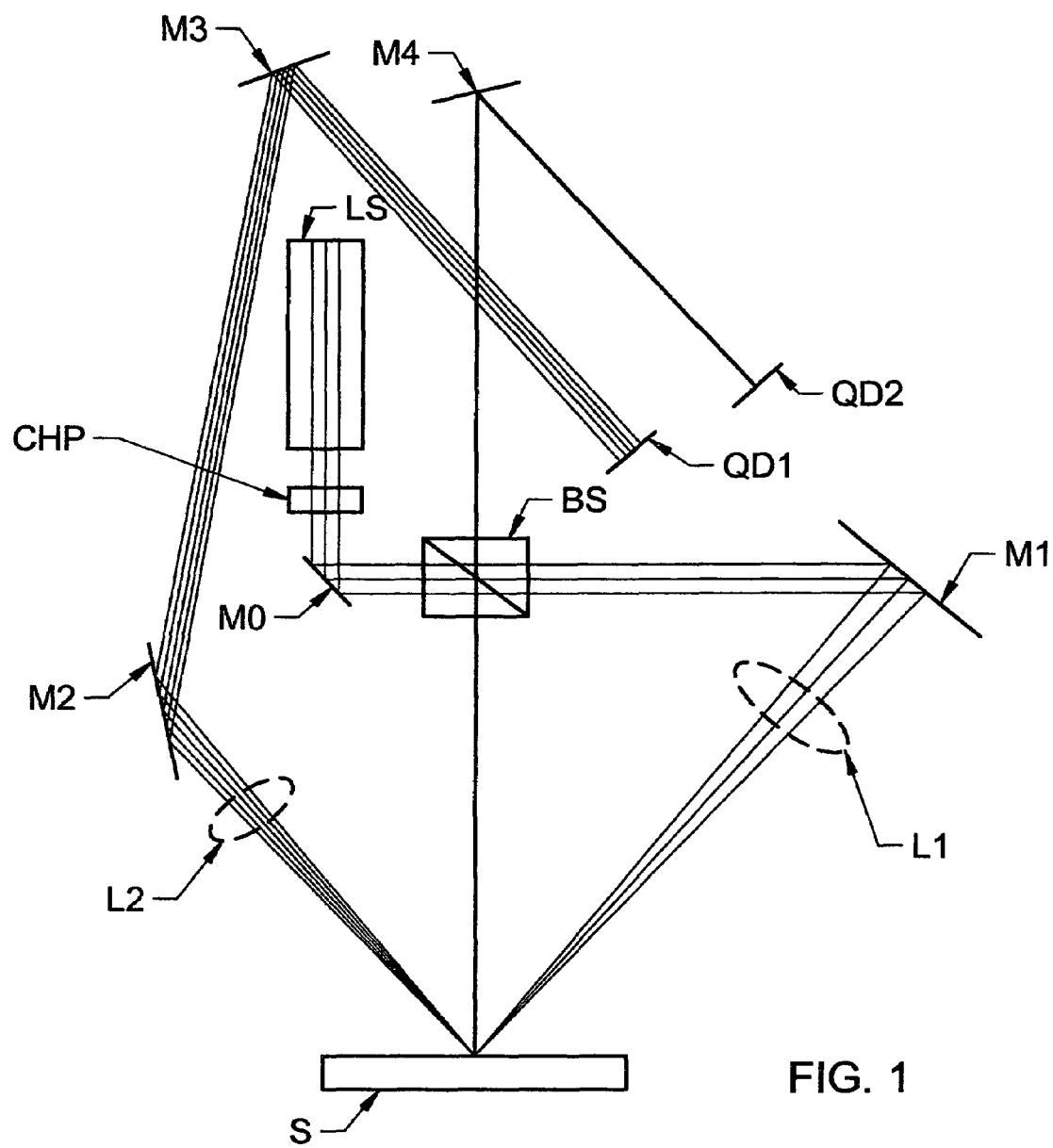
FIG. 1 shows a first embodiment of a disclosed invention sample alignment system.

Turning now to FIG. 1, a first sample alignment system embodiment comprises:
 a) a source (LS) of electromagnetic radiation;
 b) a beam splitter (BS);
 c) at least first (M1) mirror and optionally additional (eg. second (M2), third (M3) and forth (M4) mirrors);
 d) first (QD1) and second (QD2) alignment detectors;
 e) at least focusing (L1) and collimating (L2) lenses; and
 e) a stage for supporting a sample (S).

Said source (LS) of electromagnetic radiation is positioned to direct a beam of electromagnetic radiation toward said beam splitter (BS). Said beam splitter (BS) is positioned to direct a first portion of said beam toward said first mirror (M1), which reflects said first portion of said beam through said focusing lens (L1) and obliquely onto said sample (S) such that it impinges at substantially to same location at which the second portion of said beam, which is directed normally toward said sample (S), impinges. Said second portion of said beam is reflected from said sample (S) substantially directly back along the path of its incidence, through said beam splitter (BS) and into said second alignment detector (QD2). Said first portion of said beam is reflected from said sample (S), through said collimating lens (L2) and into said first alignment detector (QD1).

Said first embodiment can further comprise at least one selection from the group consisting of:
 a beam directing mirror (M0) between said light source (LS) and said beam splitter (BS);
 at least one beam directing mirror ((M2) and/or (M3)) between said collimating lens (L2) and said first alignment detector (QD1);
 at least one beam directing mirror (M4) between said beam splitter (BS) and said second alignment detector (QD2).

Figure 2:
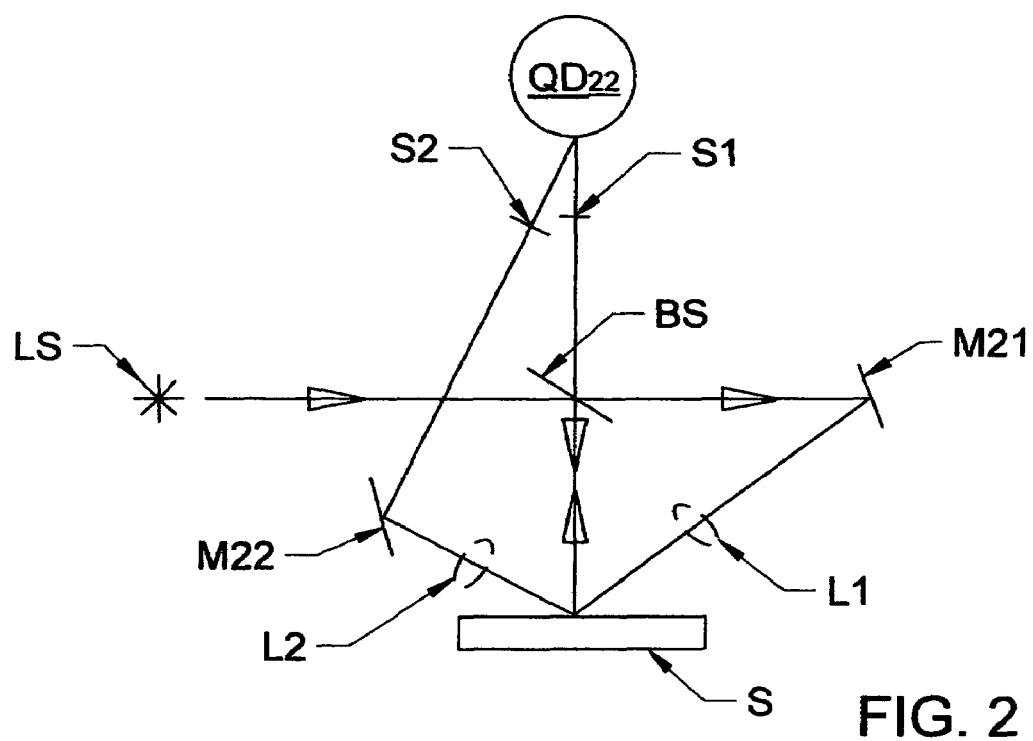
FIG. 2 shows a second embodiment of a disclosed invention sample alignment system.

Turning now to FIG. 2, a second sample alignment system embodiment comprises:
 a) a source of electromagnetism (LS);
 b) a beam splitter (BS);
 c) at least first (M21) and second (M22) mirrors;
 d) an alignment detector (QD22);
 e) first and second shutters (S1) and (S2); and
 f) a stage for supporting a sample (S).

Said beam splitter (BS) is positioned to direct a first portion of a beam of electromagnetism from said source (LS) thereof normal onto said sample (S) and a second portion thereof toward said first mirror (M21) which reflects it onto said sample (S) at an oblique angle such that it impinges thereupon at substantially the same location at which the first portion of said beam impinges. Said first portion of said beam, after normally reflecting from said sample (S) is directed back along the path of its incidence, through said beam splitter (BS) and toward said alignment detector (QD22). Said second portion of said beam, after obliquely reflecting from said sample (S), is directed to reflect from said second mirror (M22) toward said alignment detector (QD22). Said first shutter (S1) is in the pathway of said beam which passes through said beam splitter (BS) toward said alignment detector (QD22), and said second shutter (S2) is in the pathway of said beam which reflects from said second mirror (M22). In use said shutters (S1) (S2) are operated to sequentially allow entry into said alignment detector (QD22) of electromagnetic radiation:
 normally reflected from said sample (S) and directed back along the path of its incidence, through said beam splitter (BS) and toward said alignment detector (QD22); and
 obliquely reflected from said second mirror (M22) toward said alignment detector (QD22).

It is noted that focusing (L1) and collimating (L2) lenses can optionally be applied.

Figure 3:
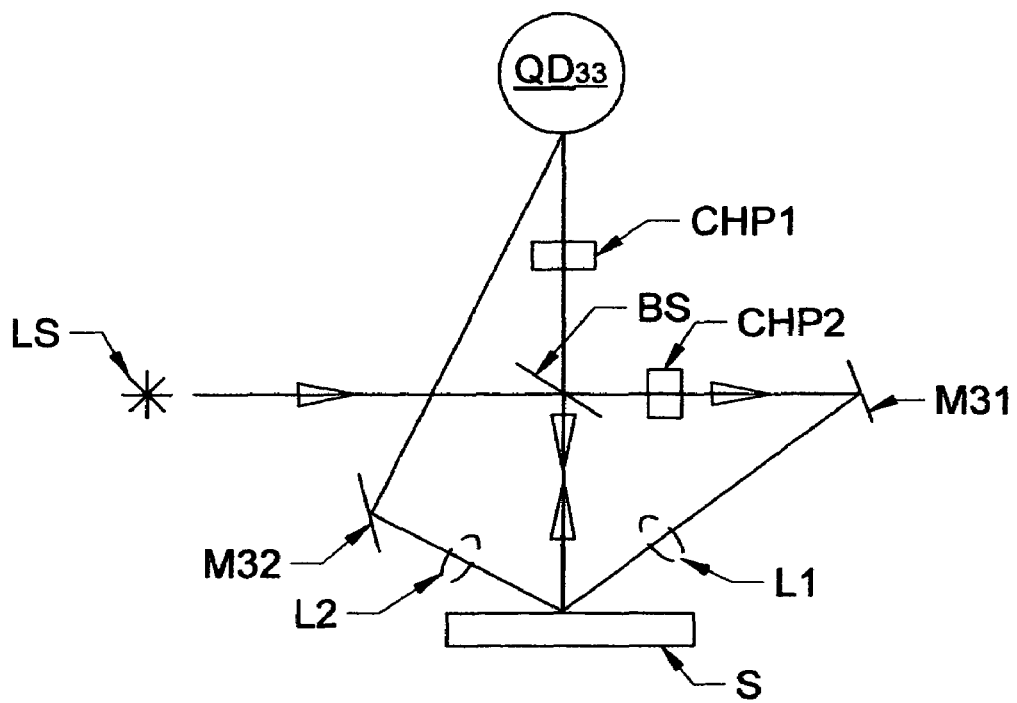
FIG. 3 shows a third embodiment of a disclosed invention sample alignment system.

Turning now to FIG. 3, a third sample alignment system embodiment comprises:
 a) a source of electromagnetism (LS);
 b) a beam splitter (BS);
 c) at least first (M21) and second (M22) mirrors;
 d) an alignment detector (QD33);
 e) first and second choppers (CHP1)) and (CHP2); and
 f) a stage for supporting a sample (s).

Said beam splitter (BS) is positioned to direct a first portion of a beam of electromagnetism from said source (LS) thereof normal onto said sample (S) and a second portion thereof toward said first mirror (M31) which reflects it onto said sample (s) at an oblique angle such that it impinges thereupon at substantially the same location at which the first portion of said beam impinges. Said first portion of said beam, after normally reflecting from said sample (S) is directed back along the path of its incidence, through said beam splitter (BS) and normally toward said sample and after reflection therefrom toward said alignment detector (QD33). Said second portion of said beam, after obliquely reflecting from said sample (S), is directed to reflect from said second mirror (M32) toward said alignment detector (QD33). Said first chopper (CHP1) is in the pathway of said beam which passes through said beam splitter (BS) toward said alignment detector (QD33), and said second chopper (CHP2) is in the pathway of said beam which passes through the beam splitter (BS) toward the first mirror (M31), and after being directed thereby to obliquely reflect from said sample (S), being directed to reflect from said second mirror (M32) toward said alignment detector (QD33). In use said choppers (CHP1) and (CHP2) are operated at different frequencies which are distinguishable by the alignment detector (QD33).

It is noted that the choppers (CHP1) and (CHP2) can be placed in any functional location in the relevant beam path way.

It is noted that focusing (L1) and collimating (L2) lenses can optionally be applied.

Figure 4:
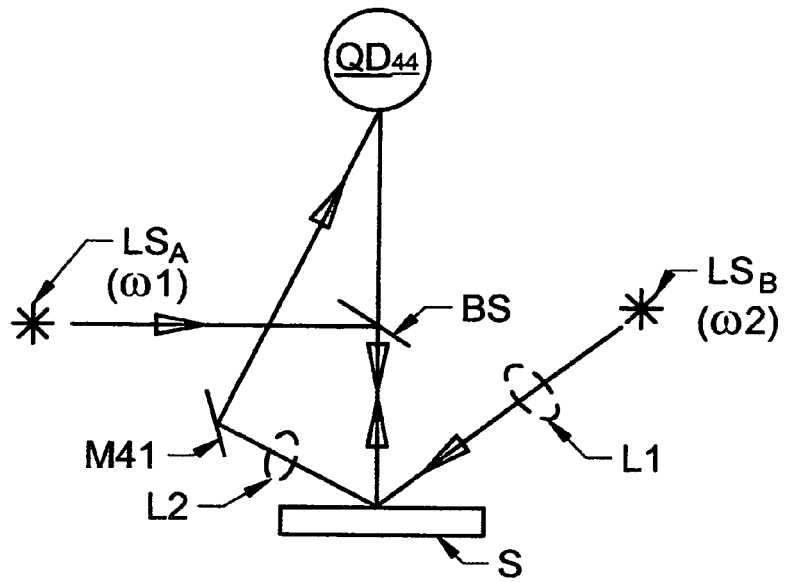
FIG. 4 shows a forth embodiment of a disclosed invention sample alignment system.

Turning now to FIG. 4, a forth sample alignment system embodiment comprises:
 a) first (LSa) and second (LSb) source of electromagnetism;
 b) a beam splitter (BS);
 c) at least a first (M41) mirror;
 d) an alignment detector (QD44);
 f) a stage for supporting a sample (S).

Said beam splitter (BS) is positioned to direct a portion of a beam of electromagnetism from said first source (LSa) thereof normal onto said sample (S). Said portion of said beam, after normally reflecting from said sample (S) is directed back along the path of its incidence, through said beam splitter (BS) and toward said alignment detector (QD44). Said second source provides a beam of electromagnetism which is directed to impinge on said sample (S) at an oblique angle such that it impinges thereupon at substantially the same location at which the first beam impinged, and after obliquely reflecting from said sample (S), is directed to reflect by said second mirror (M41) toward said alignment detector (QD44). Said first (LSa) and second (LSb) sources can produce electromagnetic radiation of different wavelengths and/or of different chopping frequencies which are separately distinguishable by the alignment detector (QD44).

It is noted that focusing (L1) and collimating (L2) lenses can optionally be applied.

Figure 5:
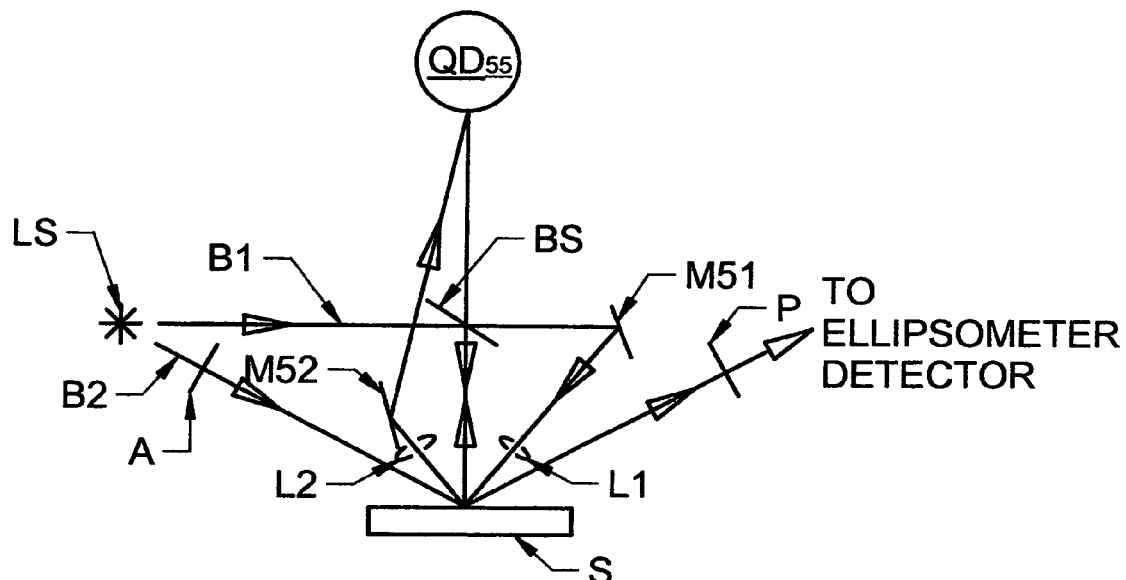
FIG. 5 shows a fifth embodiment of a disclosed invention sample alignment system.

FIG. 5 shows that a common source (LS) can be applied to provide both an ellipsometer beam and an alignment beam. This directly distinguishes over the Abraham U.S. Pat. No. 6,091,499 and it is noted that use of the same source of electromagnetic radiation for both alignment and sample analysis avoids the problem of the alignment beam being of a wavelength which does not reflect from the sample. The same wavelengths are used in alignment as are used in ellipsometric sample analysis. Said system for orienting a sample on a stage in an ellipsometer system comprises a light source (LS), a polarizer (P), said stage, an analyzer (A) and a detector;
 said system further comprises an alignment detection system with means for receiving input from said ellipsometer light source (LS), wherein said alignment detection system can detect both a tilt of a sample placed onto said stage, and a distance of said sample from said ellipsometer; and
 said system further comprising an adjusting device, wherein said adjusting device can adjust tilt of said stage, and wherein said adjusting device can adjust the relative position of said ellipsometer and alignment detection system with respect to said stage.

The alignment detection system is to be considered as including embodiments shown in FIGS. 3 and 4, and can further comprise two alignment detectors (QS1) (QD2) as indicated in FIG. 1 for receiving tilt and distance information, instead of the single detector (QD55) as shown.

It is noted that focusing (L1) and collimating (L2) lenses can optionally be applied.

In any of the foregoing sample alignment systems the alignment detector can be a multi-element detector, (eg. a Quad Detector), or can be a detector which comprises a two dimensional plurality of detection elements arranged in an array.

The systems just disclosed can be beneficially applied in ellipsometer systems which sequentially comprise a source of a beam of electromagnetism, polarizer means for imposing a state of polarization on said beam, a stage for supporting a sample, analyzer means for selecting polarization states of a beam of electromagnetic radiation after it interacts with a sample placed on said stage, and an ellipsometer detector.

It is further noted that the disclosed invention systems can be conveniently applied in automatic means for aligning the sample, wherein signals from the alignment detector(s) are used to control the vertical position and tilt of a sample.

It is also noted that where choppers are used, an ellipsometer arranged to provide a beam to the sample can be operated in ambient light instead of in a darkened environment. This can be an advantage in convenience.

Figure 6:
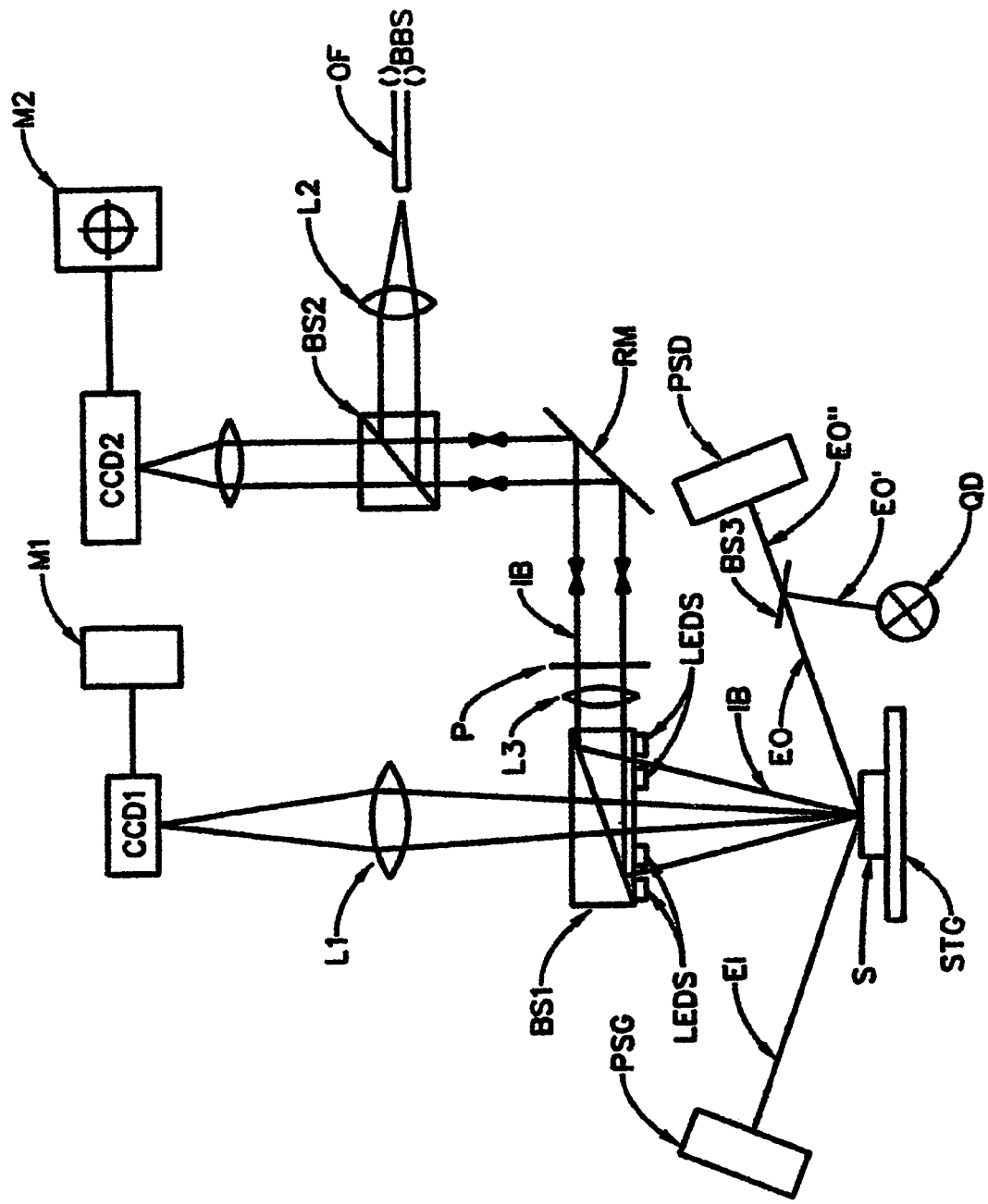
FIG. 6 is included to show a system suited to practicing a similar purpose as is the present invention, and which is Claimed in existing Applications by the same Inventor herein.

FIG. 6 is included to show a system suited to practicing a similar purpose as Claimed in other Applications by the same Inventor herein. FIG. 6 shows a system for controlling the angle of incidence at which a beam of electromagnetic radiation (EI) obliquely impinges on a monitored location of a surface of a sample (S) which is present on a sample supporting stage (STG) which can be translated in "X", "Y" and "Z" directions as well as rotated about "X", "Y" and optionally "Z" axes. Vertically, as viewed in side elevation, above said stage (STG) there is a first beam splitter means (BS1), a Zoom lens (L1) and a first camera means (CCD1) for providing a view of a portion of the surface of said sample (S), said first beam splitter (BS1) means optionally having positioned on a lower surface thereof light emitting means (LEDS) for providing light to the surface of said sample (S). Laterally with respect to said first beam splitter means (BS1) there being a reflection means (RM), and vertically above said reflection means (RM) there being a second beam splitter (BS2). Vertically above said second beam splitter (BS2) there is a second camera means (CCD2) and laterally with respect to said second beam splitter (BS2), there is sequentially a lens (L2) and an essentially point source of electromagnetic radiation which is shown as being an optical Fiber (OF) which receives electromagnetic radiation from source (BBS). Said first (CCD1) and second (CCD2) camera means each have associated therewith display means (M1) and (M2) respectively. Said system further comprises an ellipsometer polarization state generator (PSG) to cause, and a polarization stage detector (PSD) to monitor, a beam (EI) of electromagnetic radiation which in use impinges on said monitored location on said surface of said sample at an oblique angle thereto. In use said first camera means (CCD1) and its associated display means provide a view of at least a portion of the surface of a sample (S) utilizing light provided by said light emitting means (LEDS) for providing light to the surface of said sample (S) and which are positioned on said lower surface of said first beam splitter (BS1), and said essentially point source of a source of electromagnetic radiation provides electromagnetic radiation to the surface of said sample via said second beam splitter (BS2), said reflective means (R) and said first beam splitter (BS1). Said sample supporting stage (STG) is caused to be translated in any of said "X", "Y" and "Z" directions as well as rotated about said "X", "Y" and optionally "Z" axes which are necessary to cause an interrogating beam (IB) of electromagnetic radiation provided by said essentially point source, (ie. fiber optic (OF)), of a source of electromagnetic radiation to reflect from the surface of said sample (S), proceed back through said first beam splitter (BS1) means, reflect from said reflective means (R), pass through said second beam splitter means (BS2), enter said second camera means (CCD2) and cause an image on the display means (M2) associated therewith which indicates that the monitored location on the sample (S) surface is oriented so as to face substantially vertically. The purpose is to align said sample (S) surface to assure that said beam of electromagnetic radiation (EI) provided to said monitored location on the surface of said sample (S) at an oblique angle approaches said surface at a known intended angle of incidence thereto at the exact point of impingement, rather than at an angle of incidence which is modified by surface irregularities.

A problem can develop in that an interrogation beam spot can appear in the image of the first camera means (CCD1) display (M1) as part of the interrogation beam can proceed through said first beam splitter (BS1) thereinto. As a solution to this problem, said system can further provide that a polarizer means (P) be placed into the path of said interrogation beam (IB) of electromagnetic radiation provided by said essentially point source of a source of electromagnetic radiation, and in which said first beam splitter (BS1) is sensitive to polarization state. The polarizer means (P) is preferable adjustable to enable changing the direction of imposed polarization. This can be beneficial where, for instance, the sample (S) has an effect on the reflected interrogation beam (IB) polarization state, and/or where it is determined desirable to allow some of said interrogation beam to reach the first camera means (CCD1), (eg. where it is found to aid with sample surface alignment).

Note that the ellipsometer system is shown to contain a Beam Splitter (BS3) and a Quad Detector (QD). Output Beam (EO) is caused partially to enter the (PSD) as (EO") and partially enter (QD) as (EO') thereby. "X" and "Y" translation of the sample (S) which cause the (AOI) of Input Beam (EI) to reflect from said Sample (S) at various (AOI) and (POI) angles show up at the (QD). When a Sample (S) is aligned so that a normal to its surface is directed vertically in the Laboratory Frame of Reference at the location of the Ellipsometer Beam (EI) impingement thereupon small "X" and/or "Y" translations have essentially no effect on the (QD) outputs. The ellipsometer Alignment means, (ie. (BS3) and (QD)), are then utilized in the alignment procedure. Note the terminology Angle-Of-Incidence refers to the angle between the locus of a beam of electromagnetic radiation and a normal to a surface of a sample, and the terminology Plane-Of-Incidence refers to the plane formed by the Laboratory Normal the normal to the surface of the sample at and the locus of a beam of electromagnetic radiation at a location thereupon being investigated.

It is also noted that similar to the FIG. 3 Choppers (CHP1) and (CHP2), FIG. 1 shows a Chopper (CHP), and FIG. 4 indicates two Sources LSa and LSb which have associated therewith two chopping frequencies ($\omega 1$) and ($\omega 2$) respectively. The two chopping frequencies can represent means to distinguish the sources as well. The purpose of the Choppers, however, is primarily to allow use in a non-darkened room.

Having hereby disclosed the subject matter of the present invention, it should be obvious that many modifications, substitutions, and variations of the present invention are possible in view of the teachings. It is therefore to be understood that the invention may be practiced other than as specifically described, and should be limited in its breadth and scope only by the Claims.

I claim:

1. A system for use in alignment of both tilt and vertical positioning of samples comprising:
   a) a source (LS) of electromagnetic radiation;
   b) a beam splitter (BS);
   c) at least a first (M1) mirror;
   d) first (QD1) and second (QD2) alignment detectors;
   e) at least focusing (L1) and collimating (L2) lenses;
   f) a stage for supporting a sample (S); and
   g) a chopper (CHP);

said source (LS) of electromagnetic radiation being positioned to direct a beam of electromagnetic radiation toward said beam splitter (BS);

said beam splitter (BS) being positioned to direct a first portion of said beam toward said first mirror (M1), which reflects said first portion of said beam through said focusing lens (L1) and obliquely onto said sample (S) such that it impinges at substantially to same location at which the second portion of said beam, which is directed normally toward said sample (S) by said beam splitter (BS), impinges;

said second portion of said beam being reflected from said sample (S) substantially directly back along the path of its incidence, through said beam splitter (BS) and into said second alignment detector (QD2);

said first portion of said beam being reflected from said sample (S), through said collimating lens (L2) and into said first alignment detector (QD1);

and said chopper (CHP) being positioned between said light source (LS) and said beam splitter (BS) such that said beam of electromagnetic radiation directed toward said beam splitter (BS) passes therethrough and in use serves to sequentially change the intensity of said electromagnetic beam.

2. A system as in claim 1, which further comprises at least one selection from the group consisting of:
   it further comprises an adjustment means for mechanically adjusting the vertical position and tilt of said sample based upon signals from said alignment detectors; and
   it further comprises an ellipsometer system which sequentially comprise a source of a beam of electromagnetism, polarizer means for imposing a state of polarization on said beam, a stage for supporting a sample, analyzer means for selecting polarization states of a beam of electromagnetic radiation after it interacts with a sample placed on said stage, and an ellipsometer detector.

3. A system as in claim 1, which further comprises at least one selection from the group consisting of:
   a beam directing mirror (M0) between said light source (LS) and said beam splitter (BS);
   at least one beam directing mirror ((M2) and/or (M3)) between said collimating lens (L2) and said first alignment detector (QD1);

at least one beam directing mirror (M4) between said beam splitter (BS) and said second alignment detector (QD2).

4. A system as in claim 3, which further comprises at least one selection from the group consisting of:

it further comprises an adjustment means for mechanically adjusting the vertical position and tilt of said sample based upon signals from said alignment detectors; and it further comprises an ellipsometer system which sequentially comprise a source of a beam of electromagnetism, polarizer means for imposing a state of polarization on said beam, a stage for supporting a sample, analyzer means for selecting polarization states of a beam of electromagnetic radiation after it interacts with a sample placed on said stage, and an ellipsometer detector.

* * * * *